US009932645B2

(12) United States Patent
Muniesa Pérez et al.

(10) Patent No.: US 9,932,645 B2
(45) Date of Patent: Apr. 3, 2018

(54) METHOD FOR DETECTING BACTERIOLYTIC CONDITIONS IN A SAMPLE

(71) Applicant: UNIVERSITAT DE BARCELONA, Barcelona (ES)

(72) Inventors: Maria Teresa Muniesa Pérez, Barcelona (ES); Lejla Imamovic, Barcelona (ES); Elisenda Ballesté Pau, Barcelona (ES); Anicet Blanch Gisbert, Barcelona (ES); Francisco Lucena Gutiérrez, Barcelona (ES); Joan Jofre Torroella, Barcelona (ES)

(73) Assignee: UNIVERSITAT DE BARCELONA, Barcelona (ES)

( * ) Notice: Subject to any disclaimer, the term of this patent is extended or adjusted under 35 U.S.C. 154(b) by 0 days.

(21) Appl. No.: 15/036,048

(22) PCT Filed: Nov. 12, 2014

(86) PCT No.: PCT/EP2014/074383
§ 371 (c)(1),
(2) Date: May 11, 2016

(87) PCT Pub. No.: WO2015/071315
PCT Pub. Date: May 21, 2015

(65) Prior Publication Data
US 2016/0281181 A1    Sep. 29, 2016

(30) Foreign Application Priority Data
Nov. 13, 2013   (EP) ..................................... 13382459

(51) Int. Cl.
C12Q 1/70   (2006.01)
C12Q 1/10   (2006.01)
C12Q 1/34   (2006.01)
C12Q 1/04   (2006.01)

(52) U.S. Cl.
CPC ................. *C12Q 1/70* (2013.01); *C12Q 1/04* (2013.01); *C12Q 1/10* (2013.01); *C12Q 1/34* (2013.01); *G01N 2333/924* (2013.01)

(58) Field of Classification Search
None
See application file for complete search history.

(56) References Cited

U.S. PATENT DOCUMENTS 6,090,541 A     7/2000  Wicks et al.
6,436,661 B1 *  8/2002  Adams ..................... C12Q 1/04
                                                        435/34

FOREIGN PATENT DOCUMENTS

WO   WO 1994/028179        12/1994
WO      WO 9428179 A1 *    12/1994  ............... C12Q 1/34
WO   WO 2001/079528        10/2001
WO   WO 2010/065245         6/2010

OTHER PUBLICATIONS

Stomp 1992 (Histochemical localization of b-Glucuronidase; GUS Protocols: Using the Gus Gene as a Reporter of Gene Expression 103-113).*
Muniesa et al. 2003 (Bacterial Host Strains that Support Replication of Somatic Coliphages; Antonie van Leeuwenhoek 83: 305-315; see Introduction).*
Guzman, Luna C., et al., "Detection of somatic coliphages through a bioluminescence assay measuring phage mediated release of adenylate kinase and adenosine 5'-triphosphate", Journal of Virological Methods, Elsevier BV, NL, vol. 161, No. 1, Oct. 1, 2009 (Oct. 1, 2009), pp. 107-113.
Liang, W. -J., et al., "The gusBC Genes of *Escherichia coli* Encode a Glucuronide Transport System", Journal of Bacteriology, vol. 187, No. 7, Mar. 17, 2005 (Mar. 17, 2005), pp. 2377-2385.
Nnane, Daniel Ekane, et al., "Integrated analysis of water quality parameters for cost-effective faecal pollution management in river catchments", Water Research, vol. 45, No. 6, Mar. 1, 2011 (Mar. 1, 2011), pp. 2235-2246.
Lucena, F.; Jofre, J., "Potential use of bacteriophages as indicators of water quality and wastewater treatment processes." In Sabour, P.M.; Griffiths, M.W. (ed) Bacteriophages in the Control of Food and Waterborne Pathogens, ASM Press, Washington DC, 2010, pp. 103-118.
USEPA, 2006, National Primary Drinking Water Regulations: Ground Water Rule; Final Rule; 40 CFR Parts 9, 141 and 142. Federal Register, vol. 71, No. 216, pp. 65574-65660. Environmental Protection Agency. Washington DC.
Queensland Government, 2005, Water recycling guidelines. Queensland State EPA, Brisbane, Australia.
ISO 10705-2. 2000.
USEPA 2001a. Method 1602.
Muniesa, M., et al., 2003 "Bacterial host strains that support replication of somatic coliphages". Antonie van Leeuwenhoek 83: 305-315.
Guzman, et al., 2008, Evaluation of *Escherichia coli* host strain CB390 for simultaneous detection of somatic and F-specific coliphages:. Appl. Environm. Nicrobiol. 74(2): 531-534.

(Continued)

*Primary Examiner* — Mary Maille Lyons
(74) *Attorney, Agent, or Firm* — Squire Patton Boggs (US) LLP

(57) ABSTRACT

The present invention relates to a method for detecting bacteriolytic conditions in a test sample comprising the step of contacting the test sample with a bacterial strain and a substrate which undergoes a detectable change when cleaved by a specific enzyme of said bacterial strain, wherein the bacterial strain is unable of: (a) uptaking the substrate from the medium and (b) secreting the enzyme specific for the substrate outside of the cell and wherein detecting a change in the test sample due to the cleavage of the substrate by its specific bacterial enzyme indicates that bacteriolytic conditions exist in the test sample. The invention further provides a kit for performing the method of the invention.

12 Claims, 3 Drawing Sheets

(56) References Cited

OTHER PUBLICATIONS

Sambrook, J. and Russell, DW, 2001, "Molecular cloning; a laboratory manual," $3^{rd}$ ed. Cold Spring Harbor Laboratory, Cold Spring Harbor N.Y.
Muniesa, M., et al., 2006, "T Active genetic elements present in the locus of enterocyte effacement in *Escherichia coli* O26 and their role in mobility", Infect Immun 74(7): 4190-4199.
Datsenko, KA, Wanner, BL., 2000, "One-step inactivation of chromosomal genes in *Escherichia coli* K-12 using PCR products". Proc Natl Acad Sci USA 97:6640-6645.
Hanahan, D., et al., 1983, Studies on transformation of *Escherichia coli* with plasmids; Journal of Molecular Biology 166(4): 557-580.
Salter, Robert, et al., "Proposed Modifications of Environmental Protection Agency Method 1601 for Detection of Coliphages in Drinking Water, with Same-Day Fluorescence-Based Detection and Evaluation by the Performance-Based Measurement System and Alternative Test Protocol Validation Approaches", Charm Sciences Inc. 2010, vol. 76, No. 23, pp. 7803-7810.
International Search Report for PCT/EP2014/074383, dated Mar. 10, 2015 (5 pages).
International Written Opinion of the International Searching Authority for PCT/EP2014/074383 (5 pages).

\* cited by examiner

METHOD FOR DETECTING BACTERIOLYTIC CONDITIONS IN A SAMPLE

CROSS-REFERENCE TO RELATED APPLICATION

This application is a U.S. national phase entry of International Patent Application No. PCT/EP2014/074383, filed Nov. 12, 2014, which in turn claims priority to European Patent Application No. 13382459.9, filed Nov. 13, 2013. Each of the foregoing applications is incorporated herein by reference in its entirety.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "sequence listing_ST25 WOAVCRI215.txt," created May 3, 2016, and is 3930 bytes in size. The sequence listing contained in this .txt file is part of the specification and is incorporated herein by reference in its entirety.

The present invention provides a method for detecting bacteriolytic conditions, such as the presence of bacteriophages, particularly somatic coliphages, in a test sample with application in the fields of food, environmental and medical analysis.

BACKGROUND ART

Fecal pollution in water is associated with several thousand of human mortalities per day, serving as source of pathogen transmission.

A myriad of indicators are known in the art for monitoring fecal pollution, herein after also referred as "faecal contamination". In addition to classical bacterial indicators, several groups of bacteriophages (also called simply "phagues") infecting enteric bacteria have been suggested for determinating the fecal pollution level in water. Bacteriophages are viruses that infect and replicate within a bacterium. When compared to classical bacterial indicators for detection of faecal contamination, bacteriphages are more resistant to disinfection and other inactivation processes and diffuse further distances from pollution sources. Therefore, bacteriophages may serve as a better predictor of water and food quality. The potential value of bacteriophages as quality indicators in water and food has been heavily investigated and reviewed (Lucena F.; Jofre J. "Potential use of bacteriophages as indicators of water quality and wastewater treatment processes." In SABOUR, P. M.; GRIFFITHS, M. W. (ed). Bacteriophages in the Control of Food- and Waterborne Pathogens. ASM Press, Washington D.C., 2010, pag 103-118). Among bacteriophages, somatic coliphages, which are phages able to infect and replicate in *E. coli* and some bacterial species freom faecal origin closely related to *E. coli*, have recently been included in water quality guidelines, such as those for ground water in US (USEPA, 2006, National Primary Drinking Water Regulations: Ground Water Rule; Final Rule; 40 CFR Parts 9, 141 and 142. Federal Register, vol. 71, No. 216. p. 65574-65660. Environmental Protection Agency. Washington D.C.) or for water recycling in the State of Queensland in Australia (Quensland Government, 2005, Water recycling guidelines. Queensland State EPA, Brisbane. Australia).

Several strains of *E. coli* and assay media yield different results in the determination of somatic coliphages. In order to avoid this source of variability in the determination, standarized methods for detecting and quantifying this group of phages have been established and are available at present time (ISO 10705-2. 2000; APHA, AWWA and WPCF, 2001; or USEPA 2001a. Method 1602). All these standarized methods use *E. coli* C as host strain: either the wild strain ATCC13706 (APHA, 2001) or its nalidixic resistant mutants WG5 (ISO 10705-2, 2000) and CN13 (USEPA 2001a).

The APHA standard method has been however reported to perform poorly, while methods based on host strains WG5 and CN13 have shown better accuracy in water environments. Available data indicate that these *E. coli* strains are susceptible to the same bacteriophages (Muniesa et al., 2003, "Bacterial host strains that support replication of somatic coliphages". Antonie van Leeuwenhoek 83: 305-315) and, when used in the detection of somatic coliphages, they both provide similar results (Guzman et al., 2008, "Evaluation of *Escherichia coli* host strain CB390 for simultaneous detection of somatic and F-specific coliphages". Appl. Environ. Microbiol.; 74(2):531-4).

The current ISO protocol using *E. coli* WG5 for detection of somatic coliphages is a multiple-step procedure that involves coliphage replication in exponential-growth-phase cells of the host *E. coli* followed by a spotting on seeded agar for plaque confirmation. The method is laborious and time consuming, results not being available until at least 18 hours. Additionally, despite its good performance, the lack of a ready-to-use test limits the implementation of this protocol in many laboratories for general water and food management policies.

WO 9428179 A1 reports an alternative method ("Fast phage") for detecting somatic coliphages based on the measurement of phage mediated release of intracellular β-galactosidase. The method comprises incubating a coliphage-containing water sample in a medium than comprises an *E. coli* host that is susceptible to infection by coliphages. The incubation medium also contains a compound that induces the expression of high levels of intracellular beta-galactosidase in the *E. coli* host. The mixture is then incubated with a labelled substrate for beta-galactosidase, which will undergo a detectable change when cleaved by this enzyme. When the sample contains coliphages, phage-mediated lysis of the *E. coli* host releases the intracellular beta-galactosidase enzyme, which in turn cleaves the labelled substrate enabling visual detection. The method shows the great drawback of low sensitivity. In addition to requiring concentration of the sample, for detection of low phage titers the document discloses long incubation times with the labelled substrate. However, incubations exceding two hours are discouraged (possibly because longer incubations would yield high number of false positives). It follows that the method's sensitivity and specificity are unbalanced. Detecting low titers (high sensitivity) is jeopardized by false positive results (low specificity), while performing the method with high specificity inevitably leads to a bad sensitivity.

Salter introduced the "Fast Phage" concept in the standard coliphage somatic determination (EPA Method 1601) (Salter et al., 2010, "Proposed modifications of Environmental Protection Agency Method 1601 for detection of coliphages in drinking water, with same-day fluorescence-based detection and evaluation by the performance-based measurement system and alternative test protocol validation approaches"; Appl Environ Microbiol. 76(23):7803-10). The modification of the EPA method 1601 including Fast phage intended to detect low phage titers with the same performance as the standard method. Thereto, the method requires an enrichment step consisting of incubating the phage-containing sample with the *E. coli* host and beta-galactosidase inducer for at least 5 h. This step is necessary in order to increase the amount of phages in the sample. The enriched culture is then incubated with a flourescence-labelled beta-galactosidase substrate for further 3 h. The whole process implies at least 8 hours for final detection. As reported by the authors, false positive results are also an issue when peforming this method.

A different approach has been described by Guzmán (Guzman et al., 2009, "Detection of somatic coliphages through a bioluminescence assay measuring phage mediated release of adenylate kinase and adenosine 5'-triphosphate"; J Virol Methods. 161(1):107-13). The disclosed method detects somatic coliphages after phage infection of *E. coli* WG5 and lysis-mediated release of the bacterial host's adenylate kinase (AK) and adenosine 5'-triphosphate (ATP) by detection of a bioluminescent signal. This approach requires at least 3 hours for incubation of the *E. coli* host with the phage-containing sample plus the time needed to extract the AK before proceeding with the detection. Expensive laboratory equipment and reagents are required for extraction and detection of AK so that this method suffers from considerable drawbacks related to high costs and impossibility of point-of-use implementation.

In view of all the above, there is still a need to provide fast, cost-effective tests for the detection of somatic coliphages with high specificity and sensitivity.

SUMMARY OF THE INVENTION

The inventors have developed a method for the detection of bacteriophages in a test sample that overcomes the disadvantages of previous methods. The inventors have further found that this new approach may be used not only for the detection of bacteriophages, but also for detecting any other condition present in a test sample that causes the lysis of bacterial cells (herein such conditions are termed as "bacteriolytic conditions").

The inventor's approach takes advantage of a bacterial host which expresses a particular intracellular enzyme which may not be secreted to the medium and, at the same time, is unable of uptaking the substrate specific for that particular enzyme from the medium. The method comprises contacting said bacteria with the substrate specific for the particular intracellular enzyme, wherein the substrate is such that it undergoes a detectable change if cleaved by the enzyme. In the absence of bacteriolytic conditions, contact between the intracellular enzyme and its substrate is precluded, so that the enzyme may not be cleaved and no change is detected. However, in the presence of bacteriolytic conditions, the bacterial cell is lysed, releasing the enzyme to the medium where it finds and cleaves the substrate, thus inducing a detectable change in said substrate.

Thus, a first aspect of the invention relates to a method for detecting bacteriolytic conditions in a test sample comprising the step of contacting the test sample with a bacterial strain and a substrate which undergoes a detectable change when cleaved by a specific enzyme of said bacterial strain, wherein the bacterial strain is unable of: (a) uptaking the substrate from the medium and (b) secreting the enzyme specific for the substrate outside of the cell and wherein detecting a change in the test sample due to the cleavage of the substrate by its specific bacterial enzyme indicates that bacteriolytic conditions exist in the test sample.

The method allows for bacteriophage detection and, particularly, coliphage detection, with sensitivity and specificity comparable to standard ISO 10705 method (supra) in 3.5 to 4.5 h, which is a very significant reduction in assay time. Depending on the phage strain the method is able to detect 1 phage in a total time of 4.5 h, thus being the most sensitive method for detecting culturable microorganisms for the determination of faecal pollution in water. Furthermore, the invention particularly overcomes the drawbacks of the methods that rely on the "Fast Phage" principle, such as those disclosed in WO9428179 and Salter et al (supra). The inventors have observed that these methods suffer from the occurrence of high percentage of false positive results for samples containing low coliphage titers. The inventors have also observed that this lack of specificity is the result of (i) high basal signal in the absence of coliphages due to uptake of the substrate and cleavage inside the bacterial cell even in the absence of phage-mediated lysis and/or (ii) long enrichment periods which promote non-phage-related lysis. By selecting or constructing a bacterial host unable of secreting the enzyme and of uptaking the substrate the basal signal is greatly reduced, thus allowing for a sensitive detection of low phage titers without false positive results and without requiring prior concentration of the sample. These are clear advantages when compared to the method disclosed in WO9428179. Further, the method of the invention is fast, without the need of long enrichment periods such as is described in Salter et al. Finally, it does not require toxic reagents, complex manipulation of the sample, or heavy equipment, thus comprising a user-friendly and cost-effective method that allows for point-of-use detection.

The invention also provides a kit for practicing the method described above. The kit comprises reagents and means required for performing the method, particularly the bacterial host strain and enzymatic substrate which undergoes a detectable change when cleaved by the enzyme, as well as instructions to correctly perform the method. The kit of the invention may be used for point-of-use detection of bacteriolytic conditions in a test sample, for example, it may be used for in situ detection of water pollution in remote environments.

Thus, another aspect of the invention relates to a kit for performing the method as defined above comprising a bacterial strain and a substrate which undergoes a detectable change when cleaved by a specific enzyme of said bacterial strain, wherein the bacterial strain is unable of: (a) uptaking the substrate from the medium and (b) secreting the enzyme specific for the substrate outside of the cell.

Amplimer construction—Generation of three different fragments by PCR containing each uidA (primers SEQ ID NO:1-2), uidB (primers SEQ ID NO:3-5) and uidC genes (primers SEQ ID NO:4-6). Primers SEQ ID NO:5-6 present an homology region with the gene for chloramphenicol resistance (cat), which is amplified with primers SEQ ID NO:7-8.

Overlapping PCR—Once the three fragments are generated and overlapping the PCR using fragments uidB, uidC and cat as templates, a long construct is generated by PCR using primers SEQ ID NO:3-4.

Recombination—Cells WG5 are transformed with plasmid pKD46 containing the red recombinase system. The incorporation of the plasmid is confirmed with primers SEQ ID NO:11-12. The long PCR fragment containing the three fragments uidB-cat-uidC is electroporated in WG5 cells. By recombination, the fragment is inserted between uidC and uidB native genes, which are substituted by the uidC-cat-uidB fragment. The colonies incorporating the fragment have lost the uidC and uidB genes and gained chloramphenicol resistance. Cells grown in LB agar plates with cloramphenicol are confirmed by incorporation of the fragment by PCR. The plasmid pKD46 is eliminated by serial cell growth at 37° C., since this plasmid cannot replicate at this temperature.

UidA cloning. The uidA gene is amplified by PCR with primers SEQ ID NO:1-2. The fragment is ligated in a pBAD-TOPO vector that allows cloning of PCR fragments without restriction. The construct pBad::uidA is transformed in E. coli WG5 cells by electroporation. Cells containing the contruct are grown in LB agar plates with ampicillin. Complete recombinant cells are identified by selection with ampicillin and cloramphenicol, and additional PCR confirmation.

Figure 2:
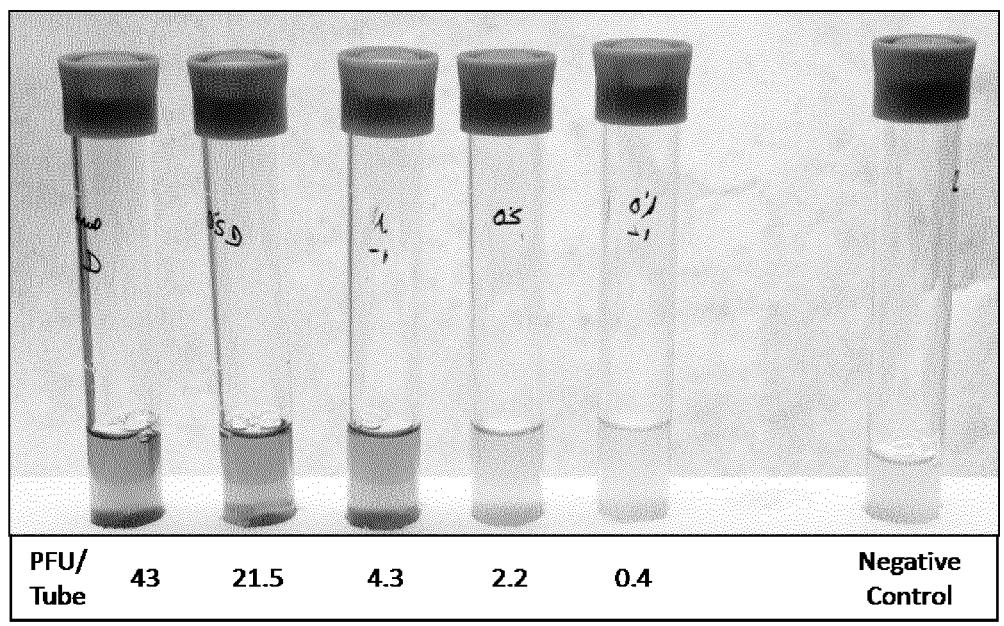

FIG. 2: Results of the different phages concentration (fpu/tub) after 3 hours of incubation. Blue color (tubes 43, 21.5 and 4.3) showed a positive result while yellow (tubes 2.2 and 0.4) indicates negative results.

Figure 3:
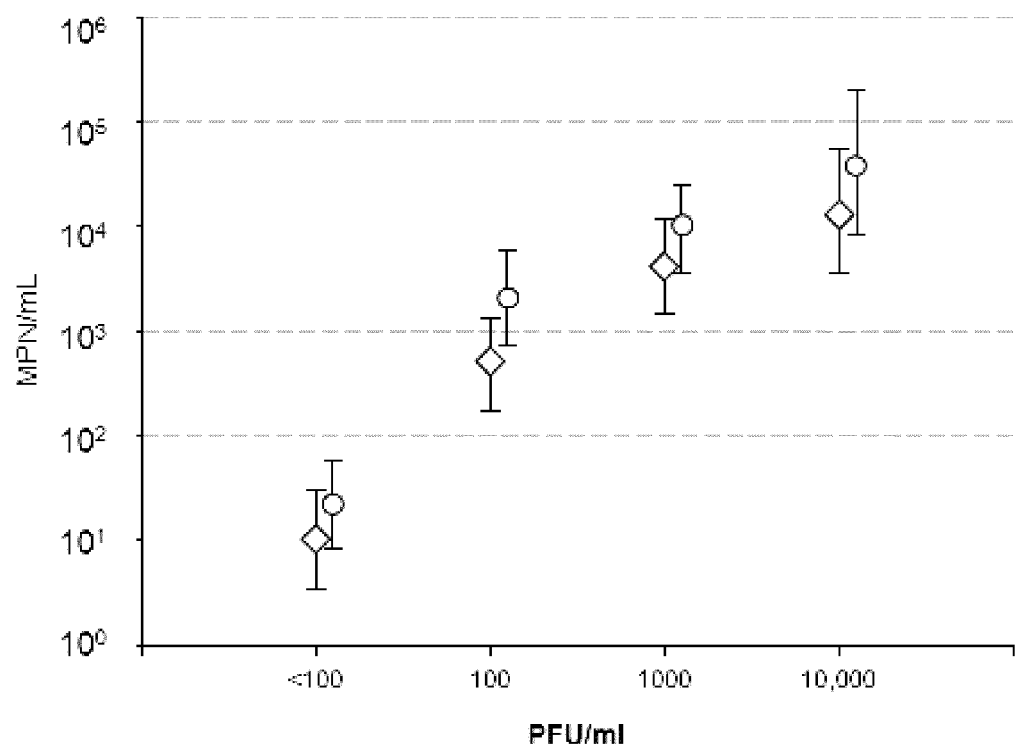

FIG. 3. Comparison between the averaged results calculated from the color test positive tubes and the positive spots showing phage lysis evaluated by the spot test. Results are calculated by Most Probable Number (MPN) for each range (<100, 100, 1000 i 10000) (pfu/ml), and show that these two calculations are not statistically different. Square: color test tube test. Circle: Lysis by spot Test.

DETAILED DESCRIPTION OF THE INVENTION

The present inventors provide a method for detecting any bacterolytic condition in a test sample by taking advantage of the lysis-mediated cleavage of a substrate when it contacts its specific bacterial enzyme. The method requires use of a bacterial strain that expresses a particular intracellular enzyme which may not be secreted to the medium and, at the same time, that is unable of uptaking the substrate specific for that particular enzyme from the medium.

The term "secreted" means transported (actively or passibly) outside of the bacterial cell through the intact cell membrane. The term "uptaken" (also named "intaken" or "internalised") means transported (actively or passibly) inside of the bacterial cell through the intact cell membrane.

The term "unable of uptaking" when referred to the bacterial strain is to be understood in the sense that the bacterial strain naturally has no mechanisms for the transport of the substrate inside the bacterial cell or, alternatively, that the bacterial strain has totally or partially inactivated transport mechanisms for uptake of the substrate. Anageoulsy, the term "unable of secreting" when referred to the bacterial strain is to be understood in the sense that the enzyme is not naturally secreted outside of the bacterial cell or, alternatively, that the bacterial strain has totally or partially inactivated secretion of the enzyme. The term "partially inactivated" is understood as a reduction of at least 75% in the uptake of the substrate or secretion of the enzyme when compared to the wild type strain. "Partially inactivated" may be 75%, 80%, 85%, 90%, 95%, 98%, or 99% of the wild type strain. "Total inactivation" refers to a reuction of 100% in the uptake of the substrate or secretion of the enzyme when compared to the wild type strain.

For sensible detection of bacteriolytic conditions the method of the invention my benefit from activating the bacterial strain in order to bring the strain into optimal metabolic conditions. Usually this activating step comprises incubating the bacterial strain in an appropriate growth medium until it reaches said optimal metabolic stage, which often coincides with logarithmic growth phase. A relevant feature of this optimal metabolic stage in the sense of the invention is the expresion of high levels of the particular enzyme selected for the detection system. In any case, the conditions for the activating step depend on the bacterial host strain. The activation step may have a duration between 2 and 18 h. Preferably the activation step takes 2 to 4 h, for example 2.5 h. It is further important that enough number of bacterial cells are activated for use in the method of the invention. The skilled person will be aware that this may be done by having a frozen or lyofilised culture of the bacterial strain which may be instantly resuspended to appropriate optical densities for use in the present invention.

The step of contacting the bacterial strain with the substrate is usually performed by incubating the test sample with the bacterial strain and the substrate for a time comprised from 10 seconds to 6 hours. In particular embodiments the contacting step is performed by incubating for a time comprised from 1 min to 5 h, or from 1 h to 4.5, 4, 3.5, 3, 2.5, 2 or 1.5 h. The skilled person will determine the appropriate contacting time depending on the bacterial strain, the substrate and, particularly, the bacteriolytic condition to be detected. For example, for bacteriophage detection this contacting time should be enough to enable infection of the bacterial cells by the bacteriophages. For detection of detergents or bacteriolytic proteins, the contacting time should be enough to enable dissolution or disruption of the bacterial wall and membrane.

Other conditions when performing the contacting step may be considered. For example, the contacting step may require incubating at a certain temperature or atmosphere, in the presence of co-factors for enzyme activity, inducers of enzyme expression, etc. For example, the temperature should be such that it supports growth of the bacterial strain. In particular embodiments the contacting step is performed at a temperature comprised from 20 to 45° C., for example 25, 30, 32, 35, 36, 37, 38, 39, 40, 41, 42, 43 or 44° C. The contacting step is also performed in the presence of an appropriate relation of bacterial cells to substrate molecules. In some embodiments bacterial cells are used in an amount such, that the optical density of the culture (measured at 600 nm) is comprised from 0.01 to 10, in particular from 0.1 to 1, and concentration of the substrate is comprised from 0.01 to 10 mg/ml, in particular, from 0.05 to 0.5 mg/ml. However, these conditions may vary. The skilled person will determine the appropriate conditions depending on the bacterial strain, the substrate and the bacteriolytic condition to be detected.

In some embodiments the bacterial strain is a genetically modified bacterial strain. A genetically modified bacterial strain is also termed "recombinant" bacterial strain. As used herein "recombinant" bacterial strain is a strain relating to, derived from, or containing genetically engineered material. In other particular embodiments the bacterial strain comprises one or both of the following modifications: (a) inactivation of the uptake of the substrate from the medium or (b) inactivation of the secretion of the enzyme specific for the substrate to the medium. The term "inactivated" is understood as total or partial inactivation. The terms "partial or total inactivation" have been defined above (see terms "partially or totally inactivated").

In the first case (a) the modifications may imply disrupting the genes responsible for the transport of the substrate across the bacterial wall and membrane. The terms "disruption" or "disruption strain" as used herein refer to a bacterial strain in which the native gene or promoter is mutated, deleted, replaced, interrupted or down regulated as to decrease the trascription of the gene. A gene can be completely (100%) down regulated by knockout or removal of the entire genomic DNA sequence. Use of a frame shift mutation, early stop codon, point mutations of critical residues, or deletions or insertions, and the like, can inactivate completely or partially the gene product by preventing or reducing transcription and/or translation of the active protein. In the second case (b), the modifications may imply disrupting the signal peptide of the enzyme.

As will be apparent to the skilled reader, option (a) of inactivating the uptake of the substrate from the medium is only required when the wild type strain naturally contains transport mechanisms for said uptake. Anageously, option (b) of inactivating the secretion of the enzyme outside of the bacterial cell is only required when the wild type strain naturally secretes the enzyme.

In other embodiments the bacterial strain is modified to display increased activity for a specific enzyme when compared to wild type strain. "increased activity" is understood as an increase of at least 110% when compared to the activity of the wild type strain. In particular embodiments the bacterial strains displays an increase of 125%, 150%, 200%, 300%, 400%, 500%, 700%, 900% or 1000% when compared to the wild type strain. Increased activity may be achieved by overexpressing the particular enzyme, such that more copies of the enzyme yield increased activity, or by modifying the gene encoding the enzyme to produce a more active form or a form that is resistant to inhibition. "Overexpression" is understood as the artificial expression of a gene in increased quantity. Overexpression can be achieved by removing repressors, adding multiple copies of the gene to the bacterial genome, upregulating the endogenous gene or introducing an exogenous vector which contains a gene encoding for the enzyme and which enables transcription of said gene inside the bacterial strain. Increased activity may also be achieved by removing inhibitors, adding activators, and the like.

Methods for up-regulating, down-regulationg or overexpressing genes are well known in the art (see, for instance, J Sambrook & D W Russell 2001, "Molecular cloning: a laboratory manual", 3rd ed. Cold Spring Harbor Laboratory, Cold Spring Harbor, N.Y.; M Muniesa et al, 2006, "T Active genetic elements present in the locus of enterocyte effacement in *Escherichia coli*O26 and their role in mobility", Infect Immun 74(7):4190-9).

In some embodiments the recombinant bacterial strain of the invention shows an overexpression of the enzyme of 110% to 1000% when compared to the wild type strain. In particular embodiments the recombinant bacterial strain of the invention shows an overexpression of the enzyme corresponding to 125%, 150%, 200%, 300%, 400%, 500%, 700% or 900% with respect to the wild type strain. In some embodiments the bacterial host does not naturally express a specific enzyme and is modified to comprise a vector which contains a gene encoding for the specific enzyme and which enables transcription of said gene inside the bacterial strain, In a particular embodiment the bacterial strain comprises a vector which contains a gene encoding for a specific enzyme and which enables transcription of said gene inside the bacterial strain, wherein the transcription of said gene is inducible. By "inducible" it is meant that transcription of the gene only takes place in the presence of a specific compound called "inducer". Non-limmiting examples of inducible vectors suitable for incorporation of the gene encoding for the enzyme are pLAC vectors (which contain a IPTG-inducible T5 promoter), rhaPBAD vectors (which contain a rhamnose-inducible promoter) and pCMV-Tet3G vectors (which contain Tetracycline-Inducible Expression Systems). When the bacterial strain contains an inducible vector for expression of the enzyme, the activating step must be performed in the presence of the inducer compound. For example, a bacterial strain which comprises a pBAD expression vector contining a gene encoding for the specific enzyme is activated in the presence of L-arabinose.

In some embodiments the enzyme contained in the bacterial strain is a glycosidase enzyme. Glycosidases (also called glycosidases or glycosyl hydrolases) are enzymes that cleave glycosidic bonds in complex sugars. Non-limmiting glycosidases which are contemplated as the enzyme of choice for the method of the invention are glycosyl hydrolases, such as beta-galactosidase, beta-glucuronidase, xylanase, lactase, amylase, chitinase, sucrase and maltase.

The substrate used in the method of the invention is any substrate that can be cleaved by one of the bacterial strain's enzymes, provided that it undergoes a detectable change when cleaved. The detectable change is any change which may be detected, for example, with the naked eye, with a spectrophotometer, fluorometer, luminometer, chromatograph, spectrometer, electrochemically, by a voltage change, or by any other means.

In some embodiments the substrate contains a colorimetric or fluorimetric moiety which is released by the action of the enzyme causing a change of color or fluorescence in the test sample. By "fluorimetric moiety", also termed "fluorimetric label", it is understood a part of a molecule which fluoresces when separated from the rest of the molecule. "Colorimetric moiety", also termed "colorimetric label", refers to part of a molecule which exhibits a color visible with the naked eye when separated from the rest of the molecule. When the substrate contains a colorimetric label the change caused by cleavage of said substrate by the enzyme may be deteced with the naked eye, enabling cost-efective and point of use implementation of the method.

In certain embodiments the substrate is a glucuronide compound, particularly, glucuronide linked by a glycosidic bond to a colorimetric or fluorimetric moiety. Glucuronide compounds are the substrate of beta-glucuronidase. The enzyme hydrolizes the glucuronide compound releasing glucuronic acid and the corresponding cleaved moiety. A particular embodiment of the invention uses 5-Bromo-4-chloro-3-indolyl beta-D-glucuronic acid cyclohexylammonium salt ($C_{20}H_{26}BrClN_2O_7$) as substrate and beta-glucuronidase as enzyme. In the art, this substrate is also known as X-Glucuronide, which term will also be used in the present application. Use of X-Glucuronide allows for colorimetric detection of bacteriolitic conditions in the sample.

Another embodiment of the invention uses 5-Bromo-6-chloro-3-indolyl beta-D-glucuronide as substrate, also for colorimetric detection. A further embodiment uses 4 methyl umbelliferyl glucuronide (MUG) as substrate, for fluorescence detection. Other embodiments use Naphthol AS-BI beta-D-glucuronide, Phenolphthalein beta-D-glucuronide sodium salt, 8-Hydroxyquinoline glucuronide or resorufin glucuronide (ReG) as substrates, each able to be detected by their particular detection system. Still a further embodiment of the invention uses p-nitrophenil beta-D-glucuronide (PNPG) as substrate, for spectrophotometric detection.

Other embodiments of the invention use galactose linked by a glycosidic bond to a colorimetric or fluorimetric moiety as substrate for beta-galactosidase enzyme. In particular embodiments the substrate is MUG (4-Methylumbelliferyl beta-D-Galactopyranoside) or X-Gal (5-bromo-4-chloro-3-indolyl-beta-D-galactoside).

Several bacteria may be used as the bacterial strain for the method of the invention. In one embodiment, the bacterial strain of the invention is a recombinant *E. coli* strain. In another embodiment the recombinant *E. coli* strain shows a reduction in the uptake of beta-glucuronidase substrate of at least 75%, in particular 80%, 85%, 90%, 95%, 98% or 100% and an over-expression of the beta-glucuronidase enzyme of at least 110%, in particular 125%, 150%, 200%, 300%, 400%, 500%, 700%, 900% or 1000%, both with respect to the wild type strain WG5 (ATCC 700078). In a further embodiment said recombinant *E. coli* strain comprises disruption of the beta-glucuronidase transporter uidB gene and/or disruption of the beta-glucuronidase trasporter uidC gene. In one embodiment, said disruption is a knock-out of uidB and/or uidC genes. In another embodiment said disrupted construct comprises a chloramphenicol resistance gene (cat) replacing a fragment of uidB and uidC genes. It is understood that the cat gene is operably linked and remains functional. The term "operably linked" as used herein refers to functionally coupled nucleic acid sequences with the aim of transcribing the protein.

In another embodiment of the invention the recombinant *E. coli* strain comprises a vector, said vector comprising a DNA sequence coding for beta-glucuronidase enzyme operably linked with regulatory elements suitable for the expression of said DNA sequence in *E. coli*. In a particular embodiment the DNA sequence coding for an *E. coli* glucuronidase is uidA gene. In a particular embodiment the uidA gene is cloned within a pBAD expression vector immediately downstream of the $P_{ara}$ inducible promoter, so that the expression of the beta-glucoronidase ase enzyme is induced by L-arabinose.

In a particular embodiment of the method of the invention, the bacterial strain is *E. coli* overexpressing uidA gene and comprising disrupted uidB and/or uidC genes, and wherein the substrate is glucuronide linked by a glycosidic bond to a colorimetric or fluorimetric moiety. In another particular embodiment the method uses X-Glucuronide as substrate and a recombinant *E. coli* strain, said recombinant *E. coli* strain having knock-out uidB and uidC genes, wherein a cat gene replaces a fragment of said uidB and uidC genes, and a vector, said vector comprising the gen uidA.

In other embodiments the bacterial strain is a *Salmonella* strain or a *Shigella* strain. The *Salmonella* or *Shigella* strains may be *S. Enterica* and *Shigella flexneri*, particularly, *salmonella* strain may be *Salmonella enterica* subsp. *enterica* serovar Typhimurium. In particular embodiments said *Salmonella* or *Shigella* strains comprise a vector, said vector comprising a DNA sequence coding for beta-glucuronidase enzyme operably linked with regulatory elements suitable for the expression of said DNA sequence in *Salmonella* or *Shigella*. In a particular embodiment the DNA sequence coding for beta-glucuronidase is uidA gene.

The method of the present invention contemplates detection of bacteriolytic conditions of any type. For instance, a bacteriolytic condition may be any type of physical, chemical or biological stress that causes lysis of bacteria. Examples of physical stress in the sense of the invention are high pressure, high temperature or mechanical friction. Examples of chemical stress include the presence of bacteriolytic chemicals, such as detergents or organic solvents (for example, chloroform and phenol). Examples of biological stress include the presence of bacteriophages, bacteriolytic proteins (such as lysozyme) or antibiotics that inhibir cell wall synthesis.

In a particular embodiment, the bacteriolytic condition to be determined by the method of the invention is the presence of bacteriophages. In another particular embodiment said bacteriophages are faecal bacteriophages. Another particular embodiment relates to detection of faecal bacteriophages in a test sample according to the invention by contacting the sample with a recombinant bacterial strain which comprises one or more of the the following modifications: (a) inactivation of the uptake of the substrate from the medium, (b) inactivation of the secretion of the enzyme specific for the substrate to the medium, c) a vector containing a gene encoding for the specific enzyme and which enables transcription of said gene inside the bacterial strain, and the contacting step being performed for a time comprised from 1 minute to 6 h. Another particular embodiment relates to detection of somatic coliphages in a test sample according to the invention by contacting the sample with glucuronide linked by a glycosidic bond to a colorimetric or fluorimetric moiety and a recombinant *E. coli* comprising disrupted uidB and/or uidC genes and/or a vector containing uidA gene which enables transcription of said gene inside the recombinant *E. coli* strain, wherein the contacting step is performed by incubating at a temperature comprised from 35 to 40° C. for a time comprised from 30 min to 6 h. Particular conditions for the contacting step for detection of faecal bacteriophages are: temperature ranging from 36 to 38° C., for example 37° C., and a time ranging from 1 to 4.5 h, for example 2.5 h.

The method of the present invention may be used for detecting bacteriolytic conditions in any type of sample. The sample may be a water sample, such as a sewater sample or sweet water sample, a sewage sludge sample and a food sample. A particularly interesting application of the present invention is to detect the presence of somatic bacteriophages in these samples in order to determine faecal contamination in the environment. The method of the invention, however, finds application in other fields, such as the medical field. For example, it may be of interest to determine the presence of antibiotics that inhibit cell wall synthesis.

The method of the invention contemplates manipulating the sample prior to contacting said sample with the bacterial host and the substrate. In this sense, the invention contemplates one or more of the following manipulations: (i) concentrating the sample, (ii) removing non-desired matter from the sample (purification), (iii) homogenisation, (iv) propagation of microorganisms. Concentration and/or purification may be achieved by filtration, centrifugation, decantation, or any other means. Homogenisation may be achieved by vortexing, agitating, use of special equipment, or any other means. By "propagation" it is meant to increase the amount of microorganism present in the sample.

A particular embodiment of the present invention refers to a method for the detection of somatic coliphages in a water sample, comprising: adding in said sample a substrate and an *E. coli* strain, said substrate being glucuronide compound (usually, glucuronide linked by a glycosidic bond to a colorimetric or fluorimetric moiety), and said *E. coli* strain showing a reduction in the intake of the said substrate of at least 75% and an over-expression of the beta-glucuronidase enzyme of at least 150%, both with respect to the wild type strain WG5 (ATCC 700078); evaluating the resulting solution of the previous step; and detecting the presence of somatic coliphages from said evaluation after a total time of between 3.5 h and 4.5 h for at least 3 phages, preferably at 3.5 h. The "total time" refers to the overall time needed to perform the method of the invention, which sums up the total incubation time including detection. In some cases the total time includes the time required for the activation step and for the contacting step. As shown in the examples below, detection of as low as 3 phages is possible within 3.5 h (2.5 h activation+1 h contacting). Thus the present method involves a significant improvement regarding the time required to detect somatic coliphages with high sensitivity and specificity.

The invention also provides a kit for performing the method described above. In a particular embodiment the kit comprises appropriate reagents for the detection of bacteriophages in a sample, said reagents comprising a substrate which is glucuronide linked by a glycosidic bond to a colorimetric or fluorimetric moiety and a *E. coli*, *Salmonella* or *Shigella* strain. Particularly, *salmonella* strain may be *Salmonella enterica* subsp. *enterica* serovar Typhimurium. In some embodiments the bacterial strains are modified as in any of the embodiments described above. In particular embodiments the kit comprises a a substrate which is glucuronide linked by a glycosidic bond to a colorimetric or fluorimetric moiety and recombinant *E. coli* strain that shows a reduction in the uptake of beta-glucuronidase substrate of 75%, 80%, 85%, 90%, 95%, 98% or 100% and an over-expression of the beta-glucuronidase enzyme of 110%, 125%, 150%, 200%, 300%, 400%, 500%, 700%, 900% or 1000%, both with respect to the wild type strain WG5 (ATCC 700078). In other embodiments the bacterial strain is *E. coli* overexpressing uidA gene and comprising disrupted uidB and/or uidC genes. In another particular embodiment the method uses X-Glucuronide as substrate and a recombinant *E. coli* strain having knock-out uidB and uidC genes, wherein a cat gene replaces a fragment of said uidB and uidC genes, and wherein the *E. coli* strain further contains a vector, said vector comprising the gen uidA. In another embodiment the kit is for the colorimetric detection of somatic coliphages in a water sample and comprises: 5-Bromo-4-chloro-3-indolyl b-D-glucuronic acid cyclohexylammonium salt; an *E. coli* strain, said strain showing a reduction in the intake of 5-Bromo-4-chloro-3-indolyl b-D-glucuronic acid cyclohexylammonium salt of at least 98%, preferably of 100%, and an over-expression of the beta-glucuronidase enzyme of at least 150% both compared with the wild type strain WG5; this *E. coli* strain being preferably a recombinant *E. coli* strain comprising an uidA gene inserted in a vector and a knock-out of uidB and uidC genes in the beta-glucuronidase operon, even more preferably comprising a cat gene replacing a fragment of said uidB and uidC genes; the kit more preferably also comprising culture media, L-arabinose, glycerol and calcium chloride.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

The standards or regulations cited are accessible and known by the person having average skill in the art and represent those most used in the art for the indicated protocols.

Materials

Modified Scholten's Broth (MSB) media (ISO 10705-2; ISO 2000) was used as basic culture media. When necessary, ampicillin (100 µg/ml) or chloramphenicol (20 µg/ml) was added to the culture media. MSB can contain 0.7% agar (semisolid MSA) or 1.4% agar (MSA). MSB was used as control culture media.

The assay medium is MSB supplemented with 0.05% of L-arabinose, 0.5% of glycerol, 15 µl CaCl 1M and 0.1 mg/ml of X-glucuronide (5-Bromo-4-chloro-3-indolyl b-D-glucuronic acid cyclohexylammonium salt; $C_{20}H_{26}BrClN_2O_7$).

Plasmid pKD46 (GenBank AY048746) for the expression of Red recombinase, was used to insert DNA fragments into the *E. coli* chromosome (Datsenko K A, Wanner B L., 2000, "One-step inactivation of chromosomal genes in *Escherichia coli* K-12 using PCR products". Proc Natl Acad Sci USA 97: 6640-6645).

Plasmid pKD3 (GenBank AY048742; Datsenko and Wanner, supra) was used to obtain the chloramphenicol acetyl transferase gene (cat) for confering resistance to chloramphenicol. All vectors were purified using the Qiagen Plasmid Midi Purification Kit (Qiagen Inc.).

The Bacteriophages in this study were used from a stock of known title containing a pure culture of one bacteriophage φX174 (ATCC 13706-B1) generated in the laboratory according to the ISO 10705-2 protocol, or with natural occurring bacteriophages from raw urban sewage or river water containing variable amounts of somatic coliphages. When using naturally occurring phages, samples were filtered through 0.22 µm pore size, low protein-binding (PES) membranes (Millipore, US) to remove bacteria and other particulate material from the samples.

PCRs were performed with a GeneAmp PCR system 2400 (Perkin-Elmer, PE Applied Biosystems). The DNA template was prepared directly from two colonies of each strain suspended in 50 µl of double-distilled water and heated to 96° C. for 10 minutes prior to addition of the reaction mixture. Purified bacterial or phage DNA was diluted 1:20 in double-distilled water. The oligonucleotides used in the invention were designed from the sequence available for *E. coli* K-12 (GenBank Accession number NC_000913).

TABLE 7

Primers

| Name | oligo | Target gene |
|---|---|---|
| SEQ ID NO: 1 UidA-For2- | CTTAATGAGGAGTCC CTT | uidA |
| SEQ ID NO: 2 UidA-Rev2. | CCAGGAGAGTTGTTG ATT | uidA |
| SEQ ID NO: 3 uidB-UP | CTGGACTGGCATGAA CTTC | uidB |
| SEQ ID NO: 4 uidC-LP | ACTTCAGCATAAAGT CATACT | uidB |
| SEQ ID NO: 5 UidB-Cm5 | AAGTATAGGAACTTC GAAGCAGCTCCAGCC TACACA*CACTGTCCA CCACTCGTCCG* | uidB overlapping cat |
| SEQ ID NO: 6 UidC-Cm3 | ACTTCGGAATAGGAA CTAAGGAGGATATTC ATATG*ACGCTGACAT TTGCACCGAT* | uidC overlapping cat |

TABLE 7-continued

Primers

| Name | oligo | Target gene |
|---|---|---|
| SEQ ID NO: 7 | Cm-5 | TGTGTAGGCTGGAGCGCTTC | cat (chloramphenicol resistance gene) |
| SEQ ID NO: 8 | Cm-3 | CATATGAATATCCTCCTTAG | cat (chloramphenicol resistance gene) |
| SEQ ID NO: 9 | pBADf | ATGCCATAGCATTTTTATCC | pBAD vector |
| SEQ ID NO: 10 | pBADr | GATTTAATCTGTATCAGG | pBAD vector |
| SEQ ID NO: 11 | RR46-UP | GAGCTCTAAGGAGGTTAT | Red recombinase pKD46 vector |
| SEQ ID NO: 12 | RR46-LP | GTGCAGTACTCATTCGTT | Red recombinase pKD46 vector |

The PCR reactions were performed as follows:

uidA. Primers SEQ ID NO:1 and SEQ ID NO:2. 95° C. 5 min. 30 cycles (95° C. 1 min, 50° C. 1.5 min, 72° C. 1 min). 72° C. 4 min.

uidB. Primers SEQ ID NO:5 and SEQ ID NO:3-3. 95° C. 5 min. 30 cycles (95° C. 1 min, 52° C. 1.0 min, 72° C. 1 min). 72° C. 4 min.

uidC. Primers SEQ ID NO:4 and SEQ ID NO:6. 95° C. 5 min. 30 cycles (95° C. 1 min, 52° C. 1.0 min, 72° C. 1 min). 72° C. 4 min.

cat: Primers SEQ ID NO:7 and SEQ ID NO:8. 95° C. 5 min. 30 cycles (95° C. 1 min, 54° C. 1.5 min, 72° C. 1 min). 72° C. 4 min.

pBAD construct confirmation: Primers SEQ ID NO:10 and SEQ ID NO:1 and primers SEQ ID NO:9 and SEQ ID NO:2. 95° C. 5 min. 30 cycles 95° C. 1 min, 48° C. 1.5 min, 72° C. 1 min). 72° C. 4 min.

pKD46: Primers SEQ ID NO:11 and SEQ ID NO:12. 95° C. 5 min. 30 cycles (95° C. 1 min, 48° C. 1 min, 72° C. 1 min). 72° C. 4 min.

Electro-competent cells were prepared from 50 ml of culture in SOB medium (super optimal broth; Hanahan D. et al., 1983, "Studies on transformation of Escherichia coli with plasmids"; Journal of Molecular Biology 166 (4): 557-580) supplemented with 0.05% L-arabinose and concentrated by centrifugation at 3000×g for 5 min. They were then washed in 4 ml of ice-cold double-distilled water. After four similar washing steps, the cells were suspended in 100 µl of ice-cold double-distilled water. The cells were mixed with the corresponding amount of DNA (plasmid or PCR-amplified, 0.5 µg) in an ice-cold microcentrifuge tube and transferred to a 0.2 cm electroporation cuvette (Bio-Rad, Inc.). The cells were electroporated at 2.5 kV with 25 F and 200 ohms resistance. After electroporation, 1 ml of SOC medium (Sambrook J. and D. W. Russellm, 2001, "Molecular cloning: a laboratory manual", 3rd ed. Cold Spring Harbor Laboratory, Cold Spring Harbor, N.Y.) was added to the cuvette. The cells were transferred to a 17 by 100 mm polypropylene tube and incubated in SOC medium at either 30° C., for temperature-sensitive plasmids, and 37° C., without shaking. Cells were concentrated ten-fold from a 1 ml culture before plating on selective media.

Modification of the Bacteria Used as Hosts.

E. coli Host

E. coli WG5 strain (ATCC 700078) recommended by the ISO standard method for the detection of somatic coliphages was genetically modified in several steps:

1) The gene encoding for the beta-glucuronidase enzyme (uidA; sequence of E. coli K-12 available in GenBank Accession number NC_000913) was amplified by PCR from E. coli WG5 with the primers identified by SEQ ID NO:1 and SEQ ID NO:2 and cloned using a pBAD-TOPO® TA Expression Kit. This kit contains a pBAD-TOPO vector that allowed the insertion of the gene under the control of an araBAD promoter (Invitrogene Corporation). Insertion of uidA was done following instructions of the manufacturer. The construct was transformed both in electrocompetent cells prepared with E. coli WG5 and in recombinant cells prepared as described below. In the resulting construct, pBAD::uidA, the gene was positioned immediately downstream of the $P_{ara}$ inducible promoter in the correct orientation, as confirmed by PCR using pBAD primers SEQ ID NO:9 and SEQ ID NO:10 and sequencing. The expression of uidA was optimized by adding L-arabinose to the medium at different final concentrations (ranging from 0 to 0.2%) as described by the manufacturer (Invitrogen Corporation). Finally, a concentration of 0.05% of L-arabinose was used. The plasmid contains an ampicillin marker, therefore the strain containing the plasmid construct was grown in the presence of ampicillin in a first stage.

Figure 1:
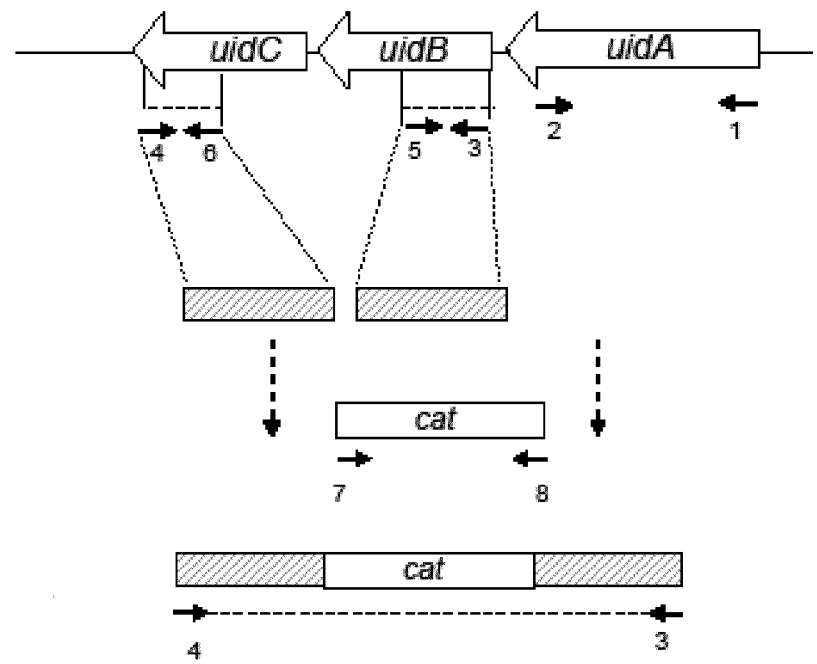
FIG. 1: Scheme of the construction of the modified strain.
Figure 1:
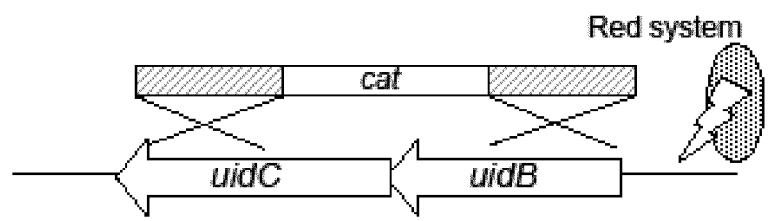
Figure 1:
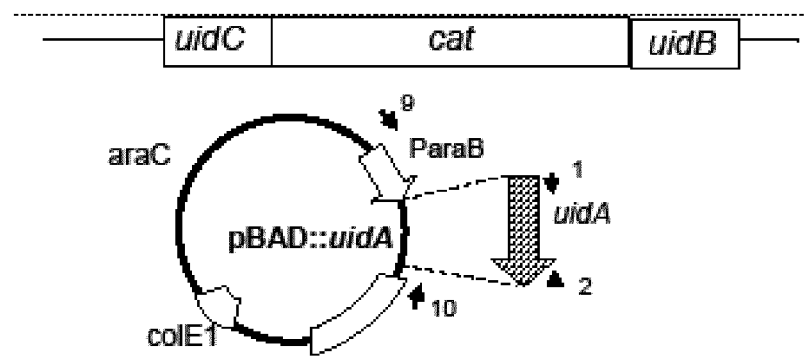

2) The construction of the amplimer containing cat gene identified by SEQ ID NO:13, which was obtained from plasmid pKD3 (GenBank AY048742), inserted within uidB and uidC genes (sequence of E. coli K-12 available in GenBank Accession number NC_000913), was performed as follows: The primer pairs Cm5-Cm3 identified by SEQ ID NO:7 and 8 were used for the amplification of the cat gene (Fragment 2: 1015 bp), at the conditions described above. Primer pairs uidB-up/uidB-Cm5, identified by SEQ ID NO:3 and SEQ ID NO:5, were used for the amplification from the uidB subunit initial codon to the 5' region of each resistance cassette (Fragment 1: 258 bp). Primers uidC-Cm3/uidClp identified by SEQ ID NO:6 and SEQ ID NO:4, were used for the amplification from the 3' region of each resistance cassette to the final codon of the uidC subunit (Fragment 3: 241 bp) (FIG. 1). The conditions used for all primer combinations were described above.

Fragments uidB and uidC were annealed at their overlapping region located in primers SEQ ID NO:5 and SEQ ID NO:6 with the cat gene They were then amplified by PCR as a single fragment with the external primers uidB-UP (SEQ ID NO:3) and uidC-LP (SEQ ID NO:4) in which the region within genes uidB-uidC was replaced by the cat gene with an annealing temperature of 50° C. and elongation time of 2 min. The fragment was then excised from the gel and purified using the Qiaquick Gel Extraction Kit (Qiagen Inc.) The final product was used for the transformation in the lysogens.

3) Plasmid pKD46 (GenBank AY048746) was transformed by electroporation as described above in the E. coli WG5 strain. This was performed in electrocompetent cells prepared from 5 ml of the culture (approximately $5 \times 10^9$ CFU/ml). Vector transformation was confirmed by PCR, using the primer pair RR46 UP/LP (SEQ ID NO:11 and SEQ ID NO:12).

4) the transformation of 30 µl of the uidB-cat-uidC fragment, corresponding to 0.1-0.5 µg of amplified DNA, containing the fragment between uidB and uidC genes truncated by the insertion of the chloramphenicol resistance gene (cat) and prepared as described above (see PCR techniques), was performed in electrocompetent cells. These cells were prepared from 50 ml cultures (approx. $5 \times 10^{10}$ CFU/ml) of the strain WG5 containing the pKD46 plasmid, grown at 30° C. in SOB medium with ampicillin and 0.05% of L-arabinose to an $OD_{600}$ of 0.6. Genes uidB and uidC were expected to be deleted by substitution through recombination of the uidB-uidC fragment by the fragment uidB-cat-uidC. After recovery in SOC medium and incubation for 4 hours, and in order to select for recombinant clones, bacteria were grown on agar medium containing chloramphenicol (20 μg/ml). Chloramphenicol resistant colonies were confirmed by PCR, using the uidB-UP-UidC-LP primers identified by SEQ ID NO:3 and SEQ ID NO:4. Cycling times and temperatures are described above. Positive colonies were also further confirmed by sequencing.

The strain was forced to lose plasmid pKD46 by growing several steps at 37° C. without ampicillin, as pKD46 cannot replicate over 30° C. The lost of the pKD46 plasmid was confirmed by PCR.

5) The recombinant lacking uidB-uidC genes WG5ΔuidBuidC::cat, was transformed with plasmid pBAD::uidA generating WG5ΔuidBuidC::cat (pBAD::uidA). This recombinant has several propierties. The transport of β-glucuronide in the strain was blocked since the transport genes were deleted. The enzyme β-glucuronidase was overexpressed in the expression vector pBAD with a promotor inducible in the presence of L-arabinose.

Salmonella and Shigella Hosts

Salmonella enterica subsp. enterica serovar Typhimurium strain WG49 (ATCC 700730) and Shigella flexneri strain 668 (clinical source) were used as host strains. Both strains were unable to transport the substrate (X-glucuronide) since they lack the genes uidB and uidC. Additionally, both strains lack uidA gene or any other gene able to use the substrate. This was confirmed by using the Chromocult Agar (Merk laboratories). The media contains the sustrate X-glucuronide that is cleaved by the enzyme β-D-glucuronidase which is characteristic for E. coli. E. coli colonies in this agar appear dark blue while Salmonella and Shigella colonies appeared negative.

Recombinant Salmonella and Shigella host strains were obtained by electro transformation of the pBAD::uidA prepared as described above in Salmonella or Shigella competent cells. Confirmation of cloning in both strains was achieved by growth of the strain in ampicillin (amp)(100 μg/ml) and by PCR using combination of primers with SEQ ID NO: 1 and SEQ ID NO: 2 (for uidA gene) and SEQ ID NO: 9 and SEQ ID NO: 10 (for the pBAD vector).

Pretreatment of Sludge and Food Samples

The samples were diluted 1/5 in PBS buffer. Sludge samples were homogenated for 5 min using a vortex or food samples were homogented using a stomacher for 30 s. The homogenate was filtered through 0.22 μm low-binding membranes (PES, Millipore). The filtrate was serial ten-fold diluted and used for the experiments as for the described method in water samples.

Example 1: Detection of Bacteriophages with Recombinant E. coli

The WG5ΔuidBuidC::cat (pBAD::uidA) was grown in standard MSB broth with ampicillin overnight at 37° C. 1 ml of the overnight culture was 1/100 diluted in fresh MSB broth with ampicillin and L-arabinose to an exponential growth phase, monitored by an optical density (OD) at 600 nm of 0.3. At this stage 0.5 ml of this activated culture was added to tubes containing 2.5 ml of assay medium (MSB containing L-arabinose, glycerol, $CaCl_2$ and X-glucuronic) and 0.1 ml of the corresponding phage suspension from the different test samples. One tube without phages was kept as control. The tubes were statically incubated at 37° C. Positive results were observed by change of colour in the tubes turning from yellow to blue after some time. The control containing the wild strain did not show any colour variation even after 6 h of incubation (FIG. 2).

Positive results obtained by the method above were confirmed by the spot test to evaluate the sensitivity of the method. Thereto, aliquots of 15 μl were extracted from the tubes after 4.5 hours of incubation and placed onto an agar monolayer prepared as described in the ISO 10705-2method containing the recombinant strain E. coli WG5ΔuidBuidC:: cat (pBAD::uidA). The plates were then incubated side up at 37° C. Those plates showing lysis in the spot area indicated that the tube contained phages. Enumeration of phages was performed by the most probable number method.

The first evaluation was that the modification in the strain did not cause a decrease in the number of phages detected. Comparison of phage counts by the ISO method between the wild type E. coli WG5 strain and the recombinant strain shown in Table 1 showed no significant differences in the densities of phages detected by both strains (Student T-test Paired Test, P<0.05).

TABLE 1

Enumeration of phages by the ISO method comparing the wild type WG5 and recombinant WG5ΔuidBuidC::cat (pBAD::uidA) as host strains

| | Source | WG5 | WG5ΔuidBuidC::cat (pBAD::uidA) | Log reduction |
|---|---|---|---|---|
| Sample Ref. | | | | |
| SWG1 | Wastewater | $4.95 \times 10^4$ | $3.80 \times 10^4$ | 0.11 |
| SWG2 | Wastewater | $7.27 \times 10^3$ | $8.56 \times 10^3$ | -0.07 |
| SWG3 | Wastewater | $1.95 \times 10^4$ | $2.06 \times 10^4$ | -0.02 |
| SWG4 | Wastewater | $7.91 \times 10^3$ | $3.34 \times 10^3$ | 0.37 |
| SWG5 | Wastewater | $7.26 \times 10^3$ | $5.12 \times 10^3$ | 0.15 |
| FW1 | River Water | $4.77 \times 10^1$ | $3.36 \times 10^1$ | 0.15 |
| ΦX174 | Laboratory | $5.70 \times 10^{10}$ | $3.20 \times 10^{10}$ | 0.25 |
| Reference: | | | | |
| Mixture of phages* | Laboratory | $2.54 \cdot 10^6$ | $2.14 \cdot 10^6$ | 0.07 |

*Mixture is composed by phage ΦX174, an environmental Siphoviridae phage and an environmental Myoviridae phage.

To further study the performance of the color test, tubes containing 0.5 ml of activated culture and 2.5 ml assay medium were inoculated at different phage concentrations from freshwater (FW) and wastewater (SW) samples, as well as from stock of phages, and were assayed using the glucuronidase color test. Each dilution of phages was assayed by triplicate. Table 2 shows those tubes showing positive results turning to blue with respect to the total number of assayed tubes, and the corresponding detection times.

TABLE 2

Results obtained by the invention's test at different phage concentrations, at incubation times of 2.5 to 4.5 hours.

| Sample | PFU/tube[1] | Positive tubes/total tubes after an incubation time of: | | |
|---|---|---|---|---|
| | | 2.5 h | 3.5 h | 4.5 h |
| FW1 | 33.6 | 3/3 | 3/3 | 3/3 |
| | 16.8 | 2/3 | 2/3 | 3/3 |
| | 3.4 | 1/3 | 1/3 | 2/3 |
| | 1.7 | 0/3 | 0/3 | 2/3 |
| | 0.3 | 0/3 | 0/3 | 1/3 |
| FW2 | 43 | 1/3 | 2/3 | 3/3 |
| | 21.5 | 1/3 | 2/3 | 3/3 |
| | 4.3 | 0/3 | 1/3 | 1/3 |
| | 2.15 | 0/3 | 0/3 | 1/3 |
| | 0.43 | 0/3 | 0/3 | 0/3 |
| SW1 | 85.6 | 3/3 | 3/3 | 3/3 |
| | 17.1 | 1/3 | 3/3 | 3/3 |
| | 8.6 | 0/3 | 3/3 | 3/3 |
| | 1.7 | 0/3 | 2/3 | 2/3 |
| | 0.9 | 0/3 | 0/3 | 1/3 |
| | 0.2 | 0/3 | 0/3 | 0/3 |
| SW2 | 33.4 | 3/3 | 3/3 | 3/3 |
| | 6.7 | 3/3 | 3/3 | 3/3 |
| | 3.3 | 2/3 | 3/3 | 3/3 |
| | 0.7 | 1/3 | 2/3 | 2/3 |
| | 0.3 | 1/3 | 1/3 | 1/3 |
| | 0.1 | 0/3 | 0/3 | 1/3 |
| Phages mixture[2] | 49.9 | 1/1 | 1/1 | 1/1 |
| | 16.6 | 1/2 | 1/2 | 2/2 |
| | 8.3 | 1/2 | 1/2 | 2/2 |
| | 1.7 | 0/2 | 0/2 | 1/2 |
| | 0.8 | 0/2 | 0/2 | 0/2 |
| | 0.5 | 0/2 | 0/2 | 0/2 |

[1]Measured after calculating the phage titer (pfus) in the water samples by ISO method.
[2]Mixture composed by phage ΦX174, one Siphoviridae phage and one Myoviridae phage.

The number of inoculated phages per tube was calculated by the ISO method. It is shown that positive results can be already obtained at 2.5 h. at higher densities of phages. At lower densities, the detection time remains within 6 hours whilst the negative control remains negative. Depending on the samples, densities as low as 1 phage/tub show positive results in at least some of the tubes. At so low densities, the chance of inoculating one single phage could vary from tube to tube.

The ratio between the numbers of phages counted according to the most probable number counted, either by colour change of the test tubes of by assessment of phage replication in the same tubes by the spot test, is shown in FIG. 3. The comparison of averaged values from the different phage densities (<$10^2$, $10^2$, $10^3$ and $10^4$ pfu/ml) (FIG. 3) showed no significant differences between both calculations at any of the ranges, indicating that the sensibility of the method is similar to that of the spot test method, although values obtained at the spot test are in all cases slightly higher than with the glucuronidase color test.

Further tests were performed to detect phages in different types of samples. In particular, sewage sludges and sewage-contaminated mussels were pre-treated as described above and tested with the color test of the invention. Table 4 shows the obtained results. The table shows phage numbers (as calculated by double agar layer method following the ISO procedure) in different dilutions from each sample and corresponding positive/negative result as obtained by the color change test (positive result: color change from yellow to blue; negative reusult: no color change).

TABLE 4 phages in sewater sludges and sewage-contaminated mussels using recombinant *E. coli*

| Sample type | Phage Fpu in samples (V = 0.5 ml) | Color test Result | Incubation t |
|---|---|---|---|
| Sewage sludge Gavà 1 | 945 | +++ | 2 h 15 min |
| | 94.5 | +++ | |
| | 9.45 | +++ | |
| Sewage sludge Gavà 2 | 515 | +++ | 2 h 28 min |
| | 51.5 | +++ | |
| | 5.15 | ++− | |
| Sewage sludge Gavà 3 | 445 | ++ | 2 h 15 min |
| | 44.5 | ++ | |
| | 4.45 | +− | |
| | 0.45 | −− | |
| Sewage-contaminated mussels 1 | 155 | +++ | 2 h 30 min |
| | 15 | +++ | |
| | 1.5 | −−− | |
| Sewage-contaminated mussels 2 | 1600 | +++ | 2 h 34 min |
| | 33.5 | +++ | |
| | 3 | −+− | |
| | <0.25 | −−− | |

+, positive result
−, negative result
Each sample was assayed in duplicate or triplicate, thus each + or − sign corresponds to one assay (+++ indicates positive for all three assays; −−− indicates negative for all three assays)

Example 3: Detection of Bacteriophages in Sewage Water with *Salmonella* and *Shigella* Strains The *Salmonella* and *Shigella* cultures containing pBAD::uidA gene were evaluated for detection of bacteriphages in sewage water.

Enumeration of phages infecting the strains was performed by the double agar method. Briefly, each strain was grown in LB+0.05% L-arabinose+amp at 37° C. to reach a densitiy of $OD_{600}$=0.3.

1 ml of each culture was mixed with 1 ml or 0.5 ml of sewage water previously filtered through 0.22 µm low-binding membranes (PES, Millipore). The mixture phage-bacteria was gently mixed with 3 ml of MSB soft agar (0.7% agar) and poured onto MSB agar plates. Plates were placed upside up until the soft agar solified and were incubated at 37° C. for 18 h. Phages were enumerated by counting lytic plaques (plaques forming units or pfu). Estimated number of phages for each bacteria was S. Typhimurium=9.34 $10^2$ pfu/ml
*Shigella flexneri*=5.10 $10^2$ pfu/ml.

0.5 ml of each dilution of the sewage water sample (direct, 1/10 and 1/100) were used to inoculate a 2.5 ml liquid culture containing MSB+substrate (5-bromo-4cloro-3indolyn-beta-D-glucorònic)+L-arabinose+glycerol+$CaCl_2$ (same liquid media used for the described method). To this mixture, 0.5 ml of *Salmonella* or *Shigella* strains grown at $OD_{600}$=0.3 were added and incubated at 37° C.

TABLE 5 phages in sewage water using recombinant *S. Typhimurium* and *Shigella flexneri*

| Bacterial strain host | Fpu in samples (V = 0.5 ml) | Color test Result | Incubation t |
|---|---|---|---|
| S. Typhimurium | 467 | + | 3.5 h |
| | 46.7 | + | |
| | 4.67 | − | |

TABLE 5-continued phages in sewage water using recombinant
*S. Typhimurium* and *Shigella flexneri*

| Bacterial strain host | Fpu in samples (V = 0.5 ml) | Color test Result | Incubation t |
|---|---|---|---|
| *Shigella flexneri* | 255 | + | 305 h |
| | 25.5 | − | |
| | 2.5 | − | |

+, positive result
−, negative result

Change of color was observed after 3.5 hours in both strains and kept until 24 hours of incubation. No change of color of the control containing no sewage samples was observed even after 24 hours of incubation.

4. Detection of Bacteriolytic Conditions Other than the Presence of Bacteriophages with *Salmonella* and *Shigella* Strains The *Salmonella* and *Shigella* cultures containing pBAD::uidA gene were evaluated for detection of other bacteriolytic conditions, in particular, sonication and heat treatments.

Sonication 0.5 ml of *Salmonella* or *Shigella* strains grown at $OD_{600}$=0.3 were added to a mixture containing MSB+substrate (5-bromo-4cloro-3indolyn-beta-D-glucorònic)+L-arabinose+glycerol+$CaCl_2$ (same liquid media used for the described method).

The sample was incubated in a ultrasound bath at room temperature for 5 minutes. After the treatment, sample was incubated at 37° C. for 24 hours. Change of colour was observed after 4 hours being more visible after 24 hours. No change in the control without treatment was observed.

Heat Treatment 0.5 ml of *Salmonella* or *Shigella* strains grown at $OD_{600}$=0.3 were added to a mixture containing MSB+substrate (5-bromo-4cloro-3indolyn-beta-D-glucorònic)+L-arabinose+glycerol+$CaCl_2$ (same liquid media used for the described method).

The sample was incubated in a bath at 90° C. for 10 minutes. After the treatment, sample was incubated at 37° C. for 24 hours. Change of color was observed after 24 hours. No change in the control without treatment was observed.

TABLE 6 detection of sonication and high temperature conditions using recombinant *S. Typhimurium* and *Shigella flexneri*

| Bacterial strain host | Bacteriolytic condition | Color test Result | Incubation t |
|---|---|---|---|
| *S. Typhimurium* | Sonication | + | 4 h |
| *S. Typhimurium* | High temperature | + | 24 h |
| *Shigella flexneri* | Sonication | + | 4 h |
| *Shigella flexneri* | High temperature | + | 24 h |

+, positive result
−, negative result

CLAUSES

1. Method for the detection of somatic coliphages in a water sample, comprising:
   a) adding in said sample a substrate and an *E. coli* strain, said substrate being a glucuronide compound comprising a detectable moiety, and said *E. coli* strain showing a reduction in the intake of the said substrate of at least 75% and an over-expression of the β-glucuronidase enzyme of at least 150%, both percentages with respect to the wild type strain *E. coli* WG5;
   b) evaluating the resulting solution of step a); and
   c) detecting the presence of somatic coliphages from the evaluation of step b) after a total time of between 3.5 and 4.5 h for at least 3 phages.

2. A method according to clause 1, comprising a purification step of the water sample before the addition of step a).

3. A method according to clauses 1 or 2, in which said glucuronide compound is 5-Bromo-4-chloro-3-indolyl b-D-glucuronic acid cyclohexylammonium salt.

4. A method according to any one of clauses 1 to 3, in which said reduction in the intake of substrate is of 98%.

5. A method according to any one of clauses 1 to 4, in which said *E. coli* strain is a recombinant *E. coli* strain.

6. A method according to clause 5, in which said recombinant *E. coli* strain comprises a disruption in the β-glucuronidase uidB gene.

7. A method according to clause 6, in which said recombinant *E. coli* strain comprises a disruption in the β-glucuronidase uidC gene.

8. A method according to clause 7, in which said disruption is a knock-out of the uidB and uidC genes.

9. A method according to clauses 7 or 8, in which said disruption comprises a cat gene replacing a fragment of UidB and UidC genes.

10. A method according to any one of clauses 5 to 9, in which said recombinant *E. coli* strain comprises a vector, said vector comprising the β-glucuronidase uidA gene.

11. A method according to any one of clauses 1 to 10, in which said evaluation of step b) is a colorimetric evaluation.

12. A method according to any one of clauses 1 to 11, in which said detection time of step c) is of 3.5 h.

13. A kit for performing the method defined in any one of clauses 1 to 12, comprising appropriate reagents for the detection of somatic coliphages in a water sample.

14. A kit for the colorimetric detection of somatic coliphages in a water sample, said kit comprising
   5-Bromo-4-chloro-3-indolyl b-D-glucuronic acid cyclohexylammonium salt; and
   an *E. coli* strain, said strain showing a reduction in the intake of 5-Bromo-4-chloro-3-indolyl b-D-glucuronic acid cyclohexylammonium salt of at least 98% and an over-expression of the β-glucuronidase enzyme of at least 150%, both percentages compared with the wild type strain WG5.

15. A kit according to clause 14, in which said *E. coli* strain is a recombinant *E. coli* strain comprising knock-out β-glucuronidase operon of uidB and uidC genes and a vector, said vector comprising an uidA gene.

REFERENCES CITED IN THE APPLICATION

Lucena F.; Jofre J. "Potential use of bacteriophages as indicators of water quality and wastewater treatment processes." In SABOUR, P. M.; GRIFFITHS, M. W. (ed). Bacteriophages in the Control of Food- and Waterborne Pathogens. ASM Press, Washington D.C., 2010, pag 103-118

USEPA, 2006, National Primary Drinking Water Regulations: Ground Water Rule; Final Rule; 40 CFR Parts 9, 141 and 142. Federal Register, vol. 71, No. 216. p. 65574-65660. Environmental Protection Agency. Washington D.C.

Quensland Government, 2005, Water recycling guidelines. Queensland State EPA, Brisbane. Australia ISO 10705-2. 2000; APHA, AWWA and WPCF, 2001; or USEPA 2001a. Method 1602

Muniesa et al., 2003, "Bacterial host strains that support replication of somatic coliphages". Antonie van Leeuwenhoek 83: 305-315

Guzman et al., 2008, "Evaluation of *Escherichia coli* host strain CB390 for simultaneous detection of somatic and F-specific coliphages". Appl. Environ. Microbiol.; 74(2): 531-4

Salter et al., 2010, "Proposed modifications of Environmental Protection Agency Method 1601 for detection of coliphages in drinking water, with same-day fluorescence-based detection and evaluation by the performance-based measurement system and alternative test protocol validation approaches"; Appl Environ Microbiol. 76(23): 7803-10

Guzman et al., 2009, "Detection of somatic coliphages through a bioluminescence assay measuring phage mediated release of adenylate kinase and adenosine 5'-triphosphate"; J Virol Methods. 161(1):107-13

J Sambrook & D W Russell 2001, "Molecular cloning: a laboratory manual", 3rd ed. Cold Spring Harbor Laboratory, Cold Spring Harbor, N.Y.

M Muniesa et al, 2006, "T Active genetic elements present in the locus of enterocyte effacement in *Escherichia coli* O26 and their role in mobility", Infect Immun 74(7): 4190-9

Datsenko K A, Wanner B L., 2000, "One-step inactivation of chromosomal genes in *Escherichia coli* K-12 using PCR products". Proc Natl Acad Sci USA 97: 6640-6645

Hanahan D. et al., 1983, "Studies on transformation of *Escherichia coli* with plasmids"; Journal of Molecular Biology 166 (4):557-580

The invention claimed is:

1. A kit for performing a method for detecting bacteriolytic conditions in a test sample, said kit comprising a bacterial strain and a substrate which undergoes a detectable change when cleaved by a specific enzyme of said bacterial strain, wherein:
   the bacterial strain is a recombinant E. coli strain that comprises a vector and a disruption or knock-out of at least one beta-glucuronidase transporter gene selected from uidB and uidC genes, wherein said vector comprises the DNA sequence of the uidA gene coding for E. coli beta-glucuronidase enzyme operably linked to regulatory elements suitable for the expression of said DNA sequence in E. coli
   the substrate is a beta-glucuronidase substrate; and
   the recombinant E. coli strain shows a reduction in the uptake of beta-glucuronidase substrate of at least 75% and an overexpression of the beta-glucuronidase enzyme of at least 110%, both with respect to the wild type strain WG5 (ATCC 700078).

2. The kit according to claim 1 for the detection of somatic coliphages in a sample.

3. The kit according to claim 1, wherein the recombinant E. coli strain shows a reduction in the uptake of beta-glucuronidase substrate of at least 98% and an overexpression of the beta-glucuronidase enzyme of at least 150%, both with respect to the wild type strain WG5 (ATCC 700078).

4. The kit according to claim 3, wherein the recombinant E. coli strain comprises disruption or knock-out of the beta-glucuronidase transporter uidB and uidC genes.

5. The kit according to claim 4, wherein the recombinant E. coli strain comprises knock-out of uidB and uidC genes.

6. The kit according to claim 1, wherein the substrate is a glucuronide linked by a glycosidic bond to a colorimetric or fluorimetric moiety.

7. The kit according to claim 6, wherein the substrate is selected from 5-Bromo-4-chloro-3-indolyl b-D-glucuronic acid cyclohexylammonium salt, 5-Bromo-6-chloro-3-indolyl beta-D-glucuronide 4 methyl umbelliferyl glucuronide (MUG), Naphthol AS-BI beta-D-glucuronide, Phenolphthalein beta-D-glucuronide sodium salt, 8-Hydroxyquinoline glucuronide, resorufin glucuronide (ReG) and p-nitrophenyl beta-D-glucuronide (PNPG).

8. The kit according to claim 1 for the detection of fecal bacteriophages in a sample.

9. A method for the detection of somatic coliphages in a water sample, comprising:
   a) providing the kit of claim 1;
   b) contacting said sample with the bacterial strain and substrate in said kit;
   c) evaluating the resulting solution of step b); and
   d) detecting the presence of somatic coliphages from the evaluation of step c) after a total time of between 3.5 and 4.5 hours for at least 3 phages.

10. A method for detecting feacal contamination in a test sample comprising detecting the presence of somatic coliphages in the test sample by the method as defined in claim 9.

11. A kit for the colorimetric detection of somatic coliphages in a water sample, said kit comprising
   (i) 5-Bromo-4-chloro-3-indolyl b-D-glucuronic acid cyclohexylammonium salt; and
   (ii) an *E. coli* strain, said strain showing a reduction in the intake of 5-Bromo-4-chloro-3-indolyl b-D-glucuronic acid cyclohexylammonium salt of at least 98% and an over-expression of the β-glucuronidase enzyme of at least 150%, both percentages compared with the wild type strain WG5,
   wherein the *E. coli* strain is a recombinant *E. coli* strain comprising a knock-out β-glucuronidase operon of uidB and uidC genes and a vector, said vector comprising an uidA gene.

12. A method for detecting bacteriolytic conditions in a test sample comprising:
   a) providing the kit of claim 11;
   b) contacting the test sample with the bacterial strain and substrate in said kit; and
   c) evaluating the test sample of step b) for a detectable change produced by cleavage of the substrate by a specific enzyme of said bacterial strain;
   wherein detecting a change in the test sample indicates that bacteriolytic conditions exist in the test sample.

* * * * *

SEQUENCE LISTING

```
<160> NUMBER OF SEQ ID NOS: 13

<210> SEQ ID NO 1
<211> LENGTH: 18
<212> TYPE: DNA
<213> ORGANISM: Artificial Sequence
<220> FEATURE:
<223> OTHER INFORMATION: UidA-For2 primer

<400> SEQUENCE: 1
cttaatgagg agtccctt                                                 18

<210> SEQ ID NO 2
<211> LENGTH: 18
<212> TYPE: DNA
<213> ORGANISM: Artificial Sequence
<220> FEATURE:
<223> OTHER INFORMATION: UidA-Rev2 primer

<400> SEQUENCE: 2
ccaggagagt tgttgatt                                                 18

<210> SEQ ID NO 3
<211> LENGTH: 19
<212> TYPE: DNA
<213> ORGANISM: Artificial Sequence
<220> FEATURE:
<223> OTHER INFORMATION: uidB-UP primer

<400> SEQUENCE: 3
ctggactggc atgaacttc                                                19

<210> SEQ ID NO 4
<211> LENGTH: 21
<212> TYPE: DNA
<213> ORGANISM: Artificial Sequence
<220> FEATURE:
<223> OTHER INFORMATION: uidC-LP primer

<400> SEQUENCE: 4
acttcagcat aaagtcatac t                                             21

<210> SEQ ID NO 5
<211> LENGTH: 56
<212> TYPE: DNA
<213> ORGANISM: Artificial Sequence
<220> FEATURE:
```

<223> OTHER INFORMATION: UidB-Cm5 primer

<400> SEQUENCE: 5
aagtatagga acttcgaagc agctccagcc tacacacact gtccaccact cgtccg    56

<210> SEQ ID NO 6
<211> LENGTH: 55
<212> TYPE: DNA
<213> ORGANISM: Artificial Sequence
<220> FEATURE:
<223> OTHER INFORMATION: UidC-Cm3 primer

<400> SEQUENCE: 6
acttcggaat aggaactaag gaggatattc atatgacgct gacatttgca ccgat    55

<210> SEQ ID NO 7
<211> LENGTH: 21
<212> TYPE: DNA
<213> ORGANISM: Artificial Sequence
<220> FEATURE:
<223> OTHER INFORMATION: Cm -5 primer

<400> SEQUENCE: 7
tgtgtaggct ggagctgctt c    21

<210> SEQ ID NO 8
<211> LENGTH: 20
<212> TYPE: DNA
<213> ORGANISM: Artificial Sequence
<220> FEATURE:
<223> OTHER INFORMATION: Cm -3 primer

<400> SEQUENCE: 8
catatgaata tcctccttag    20

<210> SEQ ID NO 9
<211> LENGTH: 20
<212> TYPE: DNA
<213> ORGANISM: Artificial Sequence
<220> FEATURE:
<223> OTHER INFORMATION: pBADf primer

<400> SEQUENCE: 9
atgccatagc atttttatcc    20

<210> SEQ ID NO 10
<211> LENGTH: 18
<212> TYPE: DNA
<213> ORGANISM: Artificial Sequence
<220> FEATURE:
<223> OTHER INFORMATION: pBADr primer

<400> SEQUENCE: 10
gatttaatct gtatcagg    18

<210> SEQ ID NO 11
<211> LENGTH: 18
<212> TYPE: DNA
<213> ORGANISM: Artificial Sequence
<220> FEATURE:
<223> OTHER INFORMATION: RR46 -UP primer

<400> SEQUENCE: 11
gagctctaag gaggttat    18

```
<210> SEQ ID NO 12
<211> LENGTH: 18
<212> TYPE: DNA
<213> ORGANISM: Artificial Sequence
<220> FEATURE:
<223> OTHER INFORMATION: RR46-LP primer

<400> SEQUENCE: 12
gtgcagtact cattcgtt                                                   18

<210> SEQ ID NO 13
<211> LENGTH: 1015
<212> TYPE: DNA
<213> ORGANISM: Artificial Sequence
<220> FEATURE:
<223> OTHER INFORMATION: Template plasmid pKD3

<400> SEQUENCE: 13
tgtgtaggct ggagctgctt cgaagttcct atactttcta gagaatagga acttcggaat      60
aggaacttca tttaaatggc gcgccttacg ccccgccctg ccactcatcg cagtactgtt     120
gtattcatta agcatctgcc gacatggaag ccatcacaaa cggcatgatg aacctgaatc     180
gccagcggca tcagcacctt gtcgccttgc gtataatatt tgcccatggt gaaaacgggg     240
gcgaagaagt tgtccatatt ggccacgttt aaatcaaaac tggtgaaact cacccaggga    300
ttggctgaga cgaaaaacat attctcaata aaccctttag ggaataggc caggttttca     360 ccgtaacacg ccacatcttg cgaatatatg tgtagaaact gccggaaatc gtcgtggtat    420
tcactccaga gcgatgaaaa cgtttcagtt tgctcatgga aaacggtgta acaagggtga    480
acactatccc atatcaccag ctcaccgtct ttcattgcca tacgtaattc cggatgagca    540
ttcatcaggc gggcaagaat gtgaataaag gccggataaa acttgtgctt attttctttt     600
acggtcttta aaaaggccgt aatatccagc tgaacggtct ggttataggt acattgagca    660
actgactgaa atgcctcaaa atgttcttta cgatgccatt gggatatatc aacggtggta    720
tatccagtga tttttttctc cattttagct tccttagctc ctgaaaatct cgacaactca    780
aaaaatacgc ccggtagtga tcttatttca ttatggtgaa agttggaacc tcttacgtgc    840
cgatcaacgt ctcatttcg ccaaaagttg gcccagggct tcccggtatc aacagggaca    900
ccaggattta tttattctgc gaagtgatct tccgtcacag gtaggcgcgc cgaagttcct    960
atactttcta gagaatagga acttcggaat aggaactaag gaggatattc atatg         1015
```